United States Patent
Labyed (10) Patent No.: US 11,647,988 B2
(45) Date of Patent: May 16, 2023

(54) ADDITIONAL DIAGNOSTIC DATA IN PARAMETRIC ULTRASOUND MEDICAL IMAGING

(71) Applicant: Siemens Medical Solutions USA, Inc., Malvern, PA (US)

(72) Inventor: Yassin Labyed, Maple Valley, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 235 days.

(21) Appl. No.: 16/687,783

(22) Filed: Nov. 19, 2019

(65) Prior Publication Data

US 2021/0145409 A1 May 20, 2021

(51) Int. Cl.
*A61B 8/08* (2006.01)
*A61B 8/00* (2006.01)

(52) U.S. Cl.
CPC .............. *A61B 8/485* (2013.01); *A61B 8/085* (2013.01); *A61B 8/463* (2013.01); *A61B 8/5223* (2013.01); *A61B 8/5246* (2013.01); *A61B 8/5292* (2013.01)

(58) Field of Classification Search
CPC ....... A61B 8/485; A61B 8/5246; A61B 8/463; A61B 8/085; A61B 8/5223
See application file for complete search history.

(56) References Cited

U.S. PATENT DOCUMENTS

| | | | |
|---|---|---|---|
| 9,468,421 B2* | 10/2016 | Benson | A61B 8/485 |
| 2004/0210136 A1* | 10/2004 | Varghese | A61B 8/445 600/443 |
| 2007/0055161 A1 | 3/2007 | Garg et al. | |
| 2014/0066759 A1 | 8/2014 | Healey | |
| 2015/0026248 A1 | 9/2015 | Kruse et al. | |
| 2015/0272547 A1* | 10/2015 | Freiburger | A61B 8/54 600/438 |
| 2016/0120502 A1* | 5/2016 | Sadeghi-Naini | A61B 8/08 600/443 |
| 2018/0289323 A1* | 10/2018 | Labyed | A61B 8/5246 |

FOREIGN PATENT DOCUMENTS

WO  2004070350  8/2004

OTHER PUBLICATIONS

International Search Report received in Corresponding International Application No. PCT/US2020/055316, dated Feb. 2, 2021.

* cited by examiner

*Primary Examiner* — Ashley K Buran
*Assistant Examiner* — Sean V Blinder (57) ABSTRACT

For parametric ultrasound imaging with an ultrasound scanner, the values for multiple parameters are determined for tissue of a patient using ultrasound. The determination may be in response to a single activation, avoiding the user having to reconfigure and activate separately for each parameter. To assist in diagnosis, one or more indicators of quality of the measurements of the parameters are calculated and displayed to the user. To further assist in diagnosis, the measurement values for the patient are displayed relative to published or population values.

18 Claims, 4 Drawing Sheets

Quantitative Ultrasound (QUS) Liver Panel

| UDFF(%) | UIS | SWS (m/s) |
|---|---|---|
| 12 | 6 | 1.4 |

Likelihood of Steatosis, Inflammation, and Fibrosis grades

|  | Low | Mild | Moderate | Severe |
|---|---|---|---|---|
| Steatosis | 12.5% | 75% | 12.5% | 0% |
| Inflammation | 10% | 10% | 40% | 40% |
| Fibrosis | 20% | 50% | 20% | 10% |

ADDITIONAL DIAGNOSTIC DATA IN PARAMETRIC ULTRASOUND MEDICAL IMAGING

BACKGROUND

The present embodiments relate to parametric ultrasound imaging. Parametric ultrasound measures a characteristic of tissue being scanned. Rather than B-mode or flow mode imaging, the scan or detected data is used to calculate the characteristic of the tissue. Parametric imaging provides quantitative values of tissue physical properties. The parametric imaging may be a biomarker characteristic derived from one or more parametrics as an indicator of normal biological processes, pathogenic processes, or response to a therapeutic intervention. Example types of parametric ultrasound imaging include quantitative imaging (e.g., non-linearity coefficient, frequency-dependent attenuation coefficient, frequency-dependent backscatter coefficient, or derived parameters such as fat fraction) and/or acoustic radiation force impulse (ARFI) imaging (e.g., shear wave speed, complex modulus of storage, complex modulus of loss, or derived parameters such as inflammation index).

In many tissues, the disease state is characterized by the presence of many conditions with varying degrees. For example, the liver can suffer from steatosis, inflammation, and fibrosis concurrently. The use of medical ultrasound to obtain a comprehensive assessment of tissue requires multi-parametric measurements of the physical properties. Quality of the calculated parameters may vary from patient-to-patient and/or for different sonographers, so the calculated values of the parameters may have variable reliability. Diagnosis may rely on unclear relationship of the calculated values to the disease state. The parametric imaging may be difficult to interpret, even for a skilled physician or sonographer. Diagnosing from multiple parameters may be even more difficult.

SUMMARY

By way of introduction, the preferred embodiments described below include methods, instructions, and systems for parametric ultrasound imaging with an ultrasound scanner. The values for multiple parameters are determined for tissue of a patient using ultrasound. The determination may be in response to a single activation, avoiding the user having to reconfigure and separately activate each parameter. To assist in diagnosis, one or more indicators of quality of the measurements of the parameters are calculated and displayed to the user. To further assist in diagnosis, the measurement values for the patient are displayed relative to published or population values.

In a first aspect, a method is provided for parametric ultrasound imaging with an ultrasound scanner. Multi-parametric ultrasound imaging of a patient is activated. The ultrasound scanner measures two or more parameters of the multi-parametric ultrasound imaging in response to one instance of activating. An image of values of the two or more parameters is generated. A quality indicator for the measuring and a relationship of one or more of the values to a population are displayed.

In a second aspect, a system is provided for parametric ultrasound medical imaging. A beamformer is configured to scan tissue in a patient with a transducer. The scan is for first and second types of the parametric ultrasound medical imaging. An image processor is configured to estimate a first value for the first type and a second value for the second type from the scan, to determine first and second indicators of quality of the estimates of the first and second values, respectively, and to generate first and second panels showing the first and second values, respectively, to published values for grades of disease states. A display is configured to display the first and second values, the first and second indicators, and the first and second panels.

In a third aspect, a method is provided for parametric ultrasound imaging with an ultrasound scanner. The ultrasound scanner measures a first tissue property and a second tissue property of the patient. An image showing the first and second tissue properties is generated. First and second indicators of reliability of the measuring of the first and second tissue properties, respectively, are displayed. First and second indicators of the measuring of the first and second tissue properties to population statistics, respectively, are displayed.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Diagnosis based on multi-parametric ultrasound imaging may benefit from determination and visualization of associated information. For simultaneous multi-parametric ultrasound imaging, different tissue properties are measured based on a single button press. An indicator for quality of each tissue property measurement is displayed. A panel indicating the measurement values relative to published values for different grades of a disease state is displayed.

Figure 1:
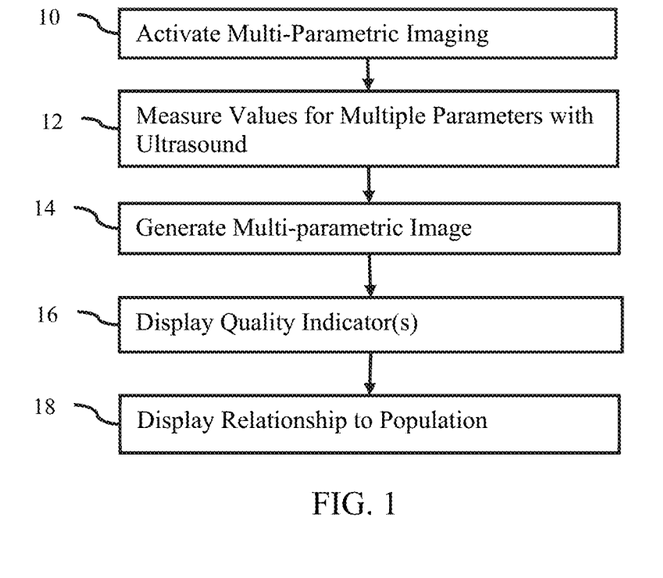
FIG. 1 is a flow chart diagram of one embodiment of a method for parametric ultrasound imaging with an ultrasound scanner.

FIG. 1 shows one embodiment of a method for parametric ultrasound imaging with an ultrasound medical scanner. Multiple types of parameters based on ultrasound imaging are used for diagnosis. Due to the variability in parametric imaging, one or more indicators of quality of the measurements are provided. To assist in understanding the results of the measurements, which may be an absolute number, the population or other study-based information may be provided with the results. The indication of quality and the relationship to other patients assists in diagnosis.

Figure 6:
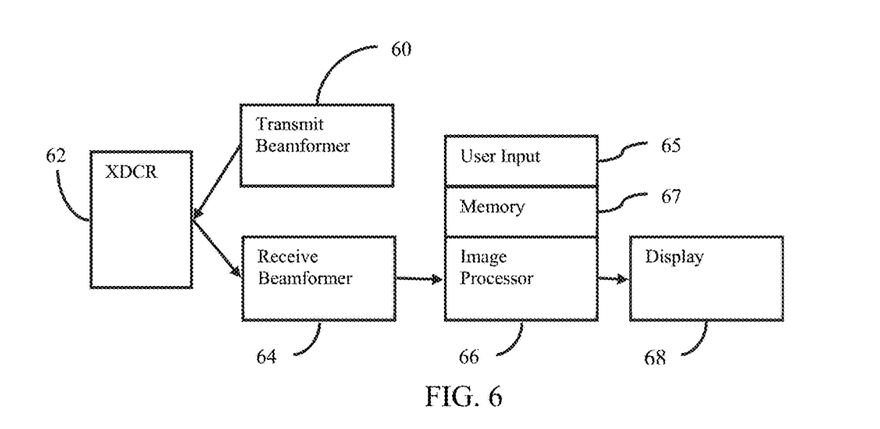
FIG. 6 is a block diagram of one embodiment of a system for multi-parametric ultrasound medical imaging.

The method is implemented by the system of FIG. 6 or a different system. A medical diagnostic ultrasound scanner performs the measurements by acoustically generating the waves and measuring the responses with a beamformer and transducer. An image processor of the scanner, computer, server, or other device estimates the values of parameters, quality indicators, and population relationship. A display device is used to output an image of the parameters, quality indicator, and/or population relationship.

Additional, different, or fewer acts may be provided. For example, one of acts 14, 16, or 18 is not provided. As another example, act 10 is not provided or is provided separately for each parameter being measured.

The acts are performed in the order described or shown (e.g., top to bottom or numerically). Other orders may be used. For example, acts 16 and 18 are performed simultaneously, such as by including the quality indicator and population relationship in a same image or display. Acts 14, 16, and 18 may be performed simultaneously or in any order. Act 14 may be performed simultaneously, before, or after acts 16 and/or 18.

In act 10, the user (e.g., sonographer) activates multi-parametric ultrasound imaging of a patient. In alternative embodiments, the ultrasound scanner activates, such as in response to detection of the tissue of interest in a scan. The transducer is positioned at a window on or in the patient for scanning the tissue of interest. For example, a handheld transducer probe is positioned against the skin of a patient on the abdomen to image the liver. Any tissue of the patient may be imaged.

The ultrasound scanner is configured for multi-parametric imaging. For example, an application for liver imaging is selected. Defaults or preset values configure the ultrasound scanner to scan the patient for measurements of multiple parameters. Alternatively, the user manually configures various programmable settings, such as beamformer or scan settings, to perform each, some, or all of the scans for multiple types of parameters.

One or a single activation is entered to cause performance of measurements of multiple, such as all, of the parameters. Rather than separately configuring and activating measurements for each parameter, one instance of activation triggers scanning for multiple types of parameters. For example, one instance of activating provides for measuring both of two tissue properties without further activation. The user presses one button, adjusts a final setting, or otherwise triggers the scanning, which is then performed for multiple (e.g., all) of the parameters of interest. Alternatively, the ultrasound scanner detects tissue of interest or other event to automatically trigger the scanning for multiple parameters based on the single or one trigger. In yet other alternatives, measurement for each parameter is separately and sequentially triggered.

In one embodiment, a single acquisition is triggered (e.g., button press or another scan trigger). The single acquisition is a sequence of scanning to measure two or more parameters without further triggering or activation by the user. Any combination of multi-parametric measurements may be performed in response to the single trigger or as part of the single acquisition. For example, one or more quantitative ultrasound measurements and corresponding scans are triggered. Example quantitative ultrasound scans may include any number, N, of fundamental frames, harmonic frames, and/or frames at different steering angles (e.g., M steering angles in M frame or M steering angles per frame). One or more ARFI measures and corresponding scans are triggered. Acoustic pushing pulses, reference position measurements, and/or tracking scans are performed in ARFI. One or more frames of data for one parameter may be used for measuring another type of parameter. For scanning to acquire multiple frames, interleaving between the scanning for different types of parameters may be used. For example, quantitative ultrasound and ARFI sequences or frames are interleaved during the single acquisition.

The ultrasound medical scanner scans the tissue of the patient. The beamformer transmits acoustic beams and/or forms receive beams from acoustic echoes. An array of elements of the transducer transduce between acoustic and electrical energies. The beamformer includes channels connected to the elements. The beamformer generates relatively delayed or phased electrical waveforms for the elements of a transmit aperture using the focus profile. The transducer converts the electrical waveforms into acoustic energy, which causes constructive interference at the focal location and along a scan line as a transmit beam. Acoustic echoes received at the elements are converted to electrical signals for the channels. The beamformer relatively delays and/or phases the electrical signals from the different elements in the receive aperture and combines the delayed or phased signals. Dynamic focusing where the focus shifts over time along a receive line by using different focus profiles due to the different locations may be used. The combination by beamforming provides beamformed samples for the various locations along receive scan lines or for receive beams. Any scan format per frame may be used, such as linear, sector, or Vector® for a region of interest for parametric ultrasound.

In act 12, the ultrasound scanner measures multiple parameters of the multi-parametric ultrasound imaging. Two or more (e.g., first and second) tissue properties are measured. The values of multiple parameters are determined for the tissue of the patient. Example tissue properties or parameters include quantitative ultrasound parameters (e.g., non-linearity coefficient, frequency-dependent attenuation coefficient, frequency-dependent backscatter coefficient, and/or derived parameters (ex: fat fraction index)) and/or ARFI parameters (e.g., shear wave speed, complex modulus (storage and/or loss) and/or derived parameters such as fibrosis). One or more parameters may be determined from quantification and ARFI measures, such as an inflammation index.

Any now known or later developed parameters may be measured. In addition or instead of B-mode, flow mode, or other non-parametric ultrasound measures, two or more types of parameters are measured. In one embodiment, liver tissue is being scanned. The parameters are any two or all three of fibrosis, inflammation, and fat fraction. These tissue properties indicate the disease state of the liver of a patient and may be measured using ultrasound scanning.

In one embodiment, an image processor estimates or measures the fat fraction of tissue of a patient. The estimation or measure is by scanning the patient. The fat fraction is specific to the patient. One or more characteristics of the patient are used to obtain the fat fraction for that patient. Some patients may have the same or similar fat fraction, but different patients may have different fat fractions. For ultrasound estimation of the fat fraction of the tissue, the ultrasound medical scanner determines the scatter and attenuation from scanning the tissue. Other combinations of quantitative ultrasound parameters may be used. The complexity of human tissue may be measured using multiple quantitative ultrasound parameters for accurate characterization of that tissue. For example, liver fat fraction is estimated using a multi-parametric approach that combines quantitative parameters extracted from the received signals of different wave phenomena, such as scattering and attenuation of longitudinal waves, propagation and attenuation of shear waves, and/or propagation and attenuation of on-axis waves from acoustic radiation force impulse (ARFI) excitation. In one embodiment, liver fat fraction is estimated by transmitting and receiving a sequence of pulses to estimate scattering parameters and by transmitting and receiving a sequence of pulses to obtain shear wave parameters. A look-up table based on empirical study may be used to relate values of the various parameters to values of fat fraction.

In another embodiment, fibrosis is estimated. Fibrosis may correlate with the shear wave speed. ARFI scanning is used to measure shear wave speed. With or without other information (e.g., patient clinical information and/or ultrasound-based information), the level or grade of fibrosis is estimated. Inflammation may be estimated from ultrasound information.

To measure the scatter, the ultrasound scanner scans the tissue with ultrasound. A sequence of transmit and receive events is performed to acquire the signals to estimate the quantitative ultrasound scatter parameters. The measure of scatter measures a tissue response to a longitudinal wave transmitted from an ultrasound scanner. The scattering or echo of the longitudinal wave impinging on the tissue is measured. Any measure of scatter may be used, such as a spectral slope of a logarithm of frequency-dependent backscatter coefficient.

The attenuation coefficient may be measured. The reference-phantom method is used, but other measures of the attenuation coefficient may be used. Acoustic energy has an exponential decay as a function of depth. A measure of acoustic intensity as a function of depth before or without depth gain correction is performed. To remove system effects, the measurement is calibrated based on measures of acoustic intensity as a function of depth in a phantom. The measurement may be subject to less noise by averaging over a one, two, or three-dimensional region. The beamformed samples or acoustic intensity may be converted to the frequency domain, and the calculation performed in the frequency domain.

The attenuation is measured as a slope of intensity as a function of depth. Other measures of attenuation may be used, such as attenuation of a shear wave over distance or time. Tissue displacement as a function of depth from an ARFI induced longitudinal wave may be used to find attenuation of the tissue. The amount of maximum displacement, displacement as a function of depth, and/or displacement as a function of time is used to calculate the attenuation. Other propagation measures may be used instead of or as the attenuation. For example, a measure of shear wave propagation or a measure of on-axis displacement (e.g., ARFI measure) is used.

The various types of parameters may be measured in response to a single trigger input. The ultrasound scanning used to measure two or more different parameters is triggered using one instance of activation. The sequence of scans used to provide the information for multiple types of parameters starts and finishes due to the one trigger event. The different sequences for the different parameters are performed in order, one after the other. Alternatively, the scanning for the different types of parameters is interleaved (e.g., interleaving scanning in a first sequence corresponding to a first parameter (e.g., fat fraction) with scanning in a second sequence corresponding to a second parameter (e.g., fibrosis)).

The measurements for the different parameters are for the same location or locations. Alternatively, the measurements for different parameters are at different locations in the same tissue and/or region of interest.

The measurements are each performed for multiple locations, such as over a spatial distribution in a region of interest. Each or multiple parameters are measured for locations distributed in one, two, or three dimensions within the patient. Alternatively, one or more (e.g., all) of the parameters are measured for one location or region. For example, fat fraction, inflammation, and/or fibrosis are measured for a single location based on user selection of that location and/or measured as one value each for a region of interest.

In act 14, the ultrasound scanner (e.g., image processor) generates an image of values of the multiple (e.g., two or more) parameters. The image is generated on a display or printer to show the multiple tissue properties of the tissue of the patient. The ultrasound scanner or a display device displays the image. In alternative embodiments, the generated image is stored or transferred over a computer network. For example, the image is transferred for storage in computerized medical record for the patient of a medical records database.

Figure 2:
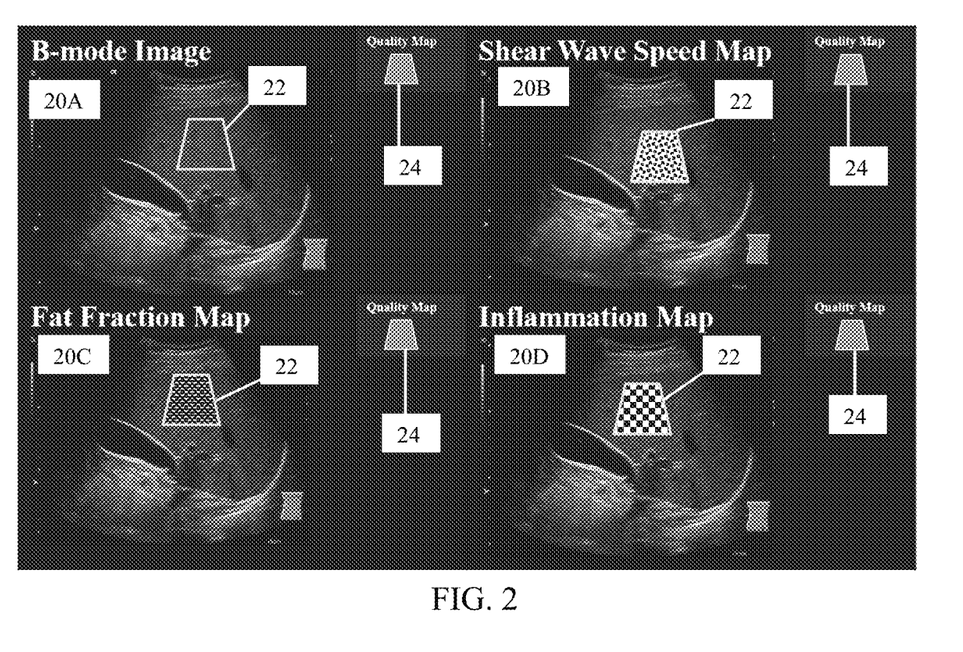
FIG. 2 illustrates an example image for multi-parametric ultrasound imaging.

The image shows the values for the different types of parameters. For example, different aspects of the image (e.g., color and grayscale or brightness) map to different parameters. The variation in color shows variation in values for one type of parameter, and the variation in brightness or grayscale shows variation in the values of another type of parameter. Alternatively, the values for the different parameters are represented in different parts of the image, such as in different sections (e.g., quads or halves) of the image. FIG. 2 shows an example with shear wave speed map 20B, fat fraction map 20C, and inflammation map 20D shown separately. A B-mode image 20A is also shown in one of the quadrants. The shear wave speed map 20B, fat fraction map 20C, and inflammation map 20D are shown as color overlays in the region of interest 22 where the rest of the spatial representation of tissue is a repeat of the B-mode image 20A. Other arrangements to show the values of the different parameters may be used.

The image represents the spatial distribution for each of the multiple parameters. Different values for a given parameters may be provided for different locations in the region of interest 22 or across the image. The values for the parameter are mapped to display values using a linear or non-linear mapping. The spatial distribution provides a one, two, or three-dimensional representation of the values of the parameter. A table or other representation of values for each parameter at multiple locations may be used. In alternative or additional embodiments, the image shows one value for each parameter. For example, a graph, colorization, and/or alphanumeric text representing the values of the parameters for a single location is generated.

Other information may be included with the image. For example, an annotation, highlighting, colorization, or overlay representing other information is provided.

The image shows both parameters simultaneously. In other embodiments, a sequence of images is generated where each image in the sequence represents the value or values for different given ones or sets of the parameters.

In acts 16 and 18, other information is determined and displayed. This other information assists in diagnosis from ultrasound scanning by the ultrasound scanner. A quality indicator for the measuring and/or a relationship of one or more of the values to a population are displayed. The other information is displayed in the image with the value or values of the different parameters or is displayed separately.

Acts 16 and 18 correspond to two different types of other information. The information of act 16 is displayed simultaneously with or separately from the information of act 18.

The display of the quality indicator and/or the relationship is as part of the image. For example, the image of FIG. 2 shows four quality indicators 24, one for each of the images and corresponding parameter and one for the B-mode image. A quality indicator may not be provided for one or more of the parameters. In other embodiments, additional quality indicators are provided for each parameter. In yet other embodiments, the relationship is displayed with the image instead of or in addition to the quality indicator. In alternative embodiments, the display of the quality indicators and relationships is separate from the image, such as displaying as part of a radiology report separate from the generated image. The relationship and quality indicator may be displayed separately or together.

In act 16, the ultrasound scanner (e.g., image processor) displays on a display one or more quality indicators. The quality indicators show an estimate or estimates of reliability of the measurements of the tissue properties.

Any number of quality indicators may be provided for any given parameter. The user may select which quality metrics to display for which parameters.

Various quality indicators may be used, such as an estimate of region of interest quality, an acquisition quality, and/or a measurement consistency quality. Any of various factors may be used for a given quality indicator. Any function, such as weighted average, may be used to combine factors for estimating the quality indicator.

For a region of interest quality, the placement of the region of interest relative to tissue of the patient is used to indicate quality prior and/or after measuring the parameters. The homogeneity of the tissue in the region of interest (e.g., lack of variance), presence of vessels, and/or position relative to one or more landmarks (e.g., relative to a liver capsule or segment 8 of the liver) may be used.

For an acquisition quality indicator, the quality of the ultrasound data acquired for the parameters is estimated. The estimation occurs after acquiring the scan data. The signal-to-noise ratio (SNR), usable frequency band (e.g., range of frequency sufficiently sampled in the acquisition), and/or deviation from a linear or other fit to the data may indicate quality of the acquisition. Insufficient transducer contact, motion, shadows, clutter noise, transducer malfunction, or other source of error in acquisition may be estimated.

For measurement consistency, the quality of the value of the parameter is estimated. After estimation of the parameter, the quality of the estimate is determined. The variability of the measurement within the region of interest (e.g., due to tissue heterogeneity) and/or variability due to different scan angles (e.g., due to tissue anisotropy) are used.

The quality indicators are based on experiments, a mathematical function, statistics, or other information. For example, fuzzy logic is used to determine quality. In this method, a membership function for each parameter is empirically defined (e.g. SNR, maximum displacement), and the outputs of each membership function given the input parameters at a location are summed to generate the likelihood of quality. The maximum value of the sum corresponds to the quality to be assigned. As another example, machine learning from a collection of training samples or data with known ground truth regarding the quality is used to determine statistics or a matrix function for quality. A probability function indicates the likelihood of each quality for a given location, and the quality with the highest probability is selected. The quality determination is performed using a lookup table, fuzzy logic function, programmed function, or matrix function.

The quality for each location relies on data for that location and not data for other locations. In alternative embodiments, spatial filtering or information from adjacent locations may be used for classifying quality for a given location.

The quality indicator or indicators are displayed as a map representing quality as a function of location. The quality at different locations is shown. FIG. 2 shows an example, where a small map 24 of the region of interest shows a selected quality by location. The estimated quality by location is mapped to color, grayscale, brightness, or another characteristic of the miniaturized map 24. Larger or smaller spatial representations may be used. The map 24 may be interactive, such as where the map 24 is enlarged by hovering or clicking on the map 24. Separate maps 24 may be provided for separate quality indicators. Alternatively, one quality indicator is used for each parameter or the displayed quality indicator is a combination of a plurality of quality scores for the parameter.

Figure 3:
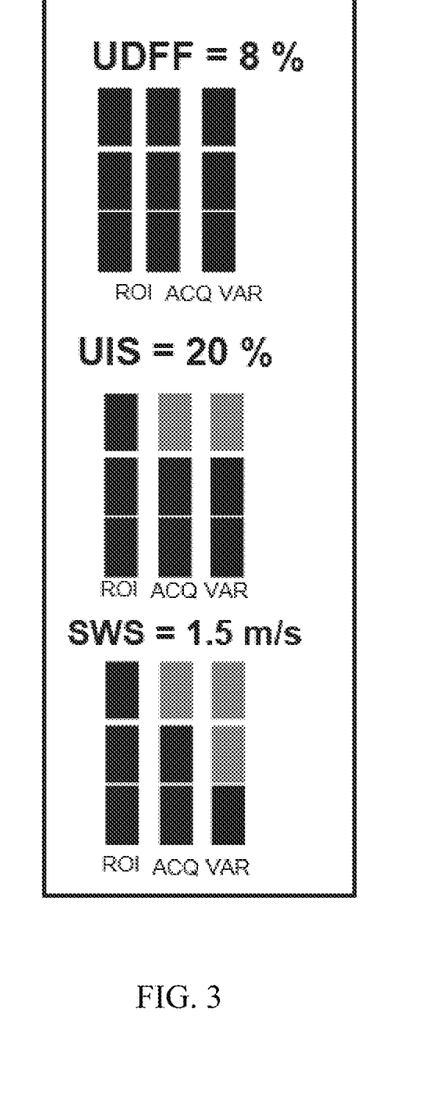
FIG. 3 illustrates example display of quality indicators.

In another embodiment, the quality indicator is a bar, graph, chart, or alphanumeric text. FIG. 3 shows an example where quality is provided for one location or for the region of interest. The measurement for the location or region is given for each parameter. UDFF is ultrasound-derived fat fraction, UIS is ultrasound inflammation score, and SWS is shear wave speed. For each of these parameters, three quality indicators are provided—region of interest (ROI), acquisition (ACQ), and variance or consistence (VAR). The coloring or grayscale of the bars indicates the estimate of quality. For example, the VAR quality indicator for SWS is low while ROI and ACQ are high. Three levels of quality (low, medium, high) are provided. Other level resolutions may be used.

In act 18, the ultrasound scanner (e.g., image processor) displays on a display one or more relationships of the measurements to a population or published statistics. The relationship shows where along the disease spectrum the value of the parameter measured for a patient falls. The statistics from other sources may reflect grading or indexing of severity of the disease. By displaying the relationship, the severity for a given patient is represented in a way that communicates more information for diagnosis. More than the absolute measure is provided to assist review of the ultrasound imaging.

Figure 4:
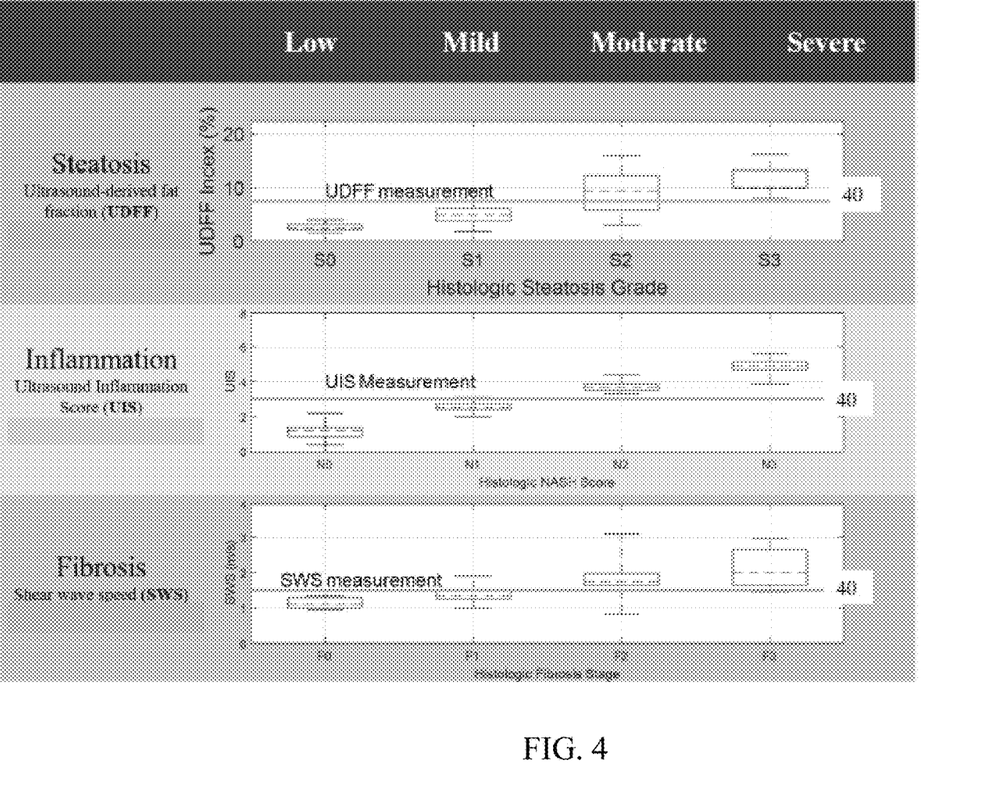
FIG. 4 illustrates one embodiment of a display of relationship to population.

An indication of the relationship of the measured tissue properties to the population statistic is displayed. Any of various display formats may be used. In one embodiment, a histologic grading is used. FIG. 4 shows an example boxplot of histologic grading for a liver assessment. The measured parameters or tissue properties are UDFF, UIS, and SWS. The horizontal line 40 for each parameter represents the ultrasound measured value for that tissue property. The disease states are divided into low, mild, moderate, and severe, but other divisions may be used. For each state, a box of the represents the 50% range (e.g., 25%-75% of cases) with a dashed horizontal line showing the median, and the whiskers represent the maximum and minimum values for the state. Other boxplot or histologic grading representations of the relationship (e.g., value of the measurement for the patient to population statistics) may be used.

The population information is from an available grouping, such as patients examined for each disease in a hospital, in a region, or as part of a study. For example, published meta-analysis data is used. The data from one or more studies or trials is aggregated to determine the statistics for the disease states.

In another embodiment, the relationship indicates the measured value relative to a receiver operating characteristic (ROC) curve. The population statistical information is used to form the ROC curve. The relationship is provided by plotting where along the ROC curve the measured value is located.

In yet another embodiment, the relationship is displayed as a probability of membership. The population information indicates ranges of values for each state of the disease. A Bayesian analysis is used to compute the likelihood functions. For example, the likelihood functions are P(Steatosis Grade|UDFF)=P(UDFFS|tenosis Grade)×P(Steatosis Grade)/P(UDFF); P(Inflammation Grade|UIS)=P(UIS|Inflammation Grade)×P(Inflammation Grade)/P(UIS); and P(Fibrosis Grade|SWS)=P(SWS|Fibrosis Grade)×P(Fibrosis Grade)/P(SWS).

Figure 5:
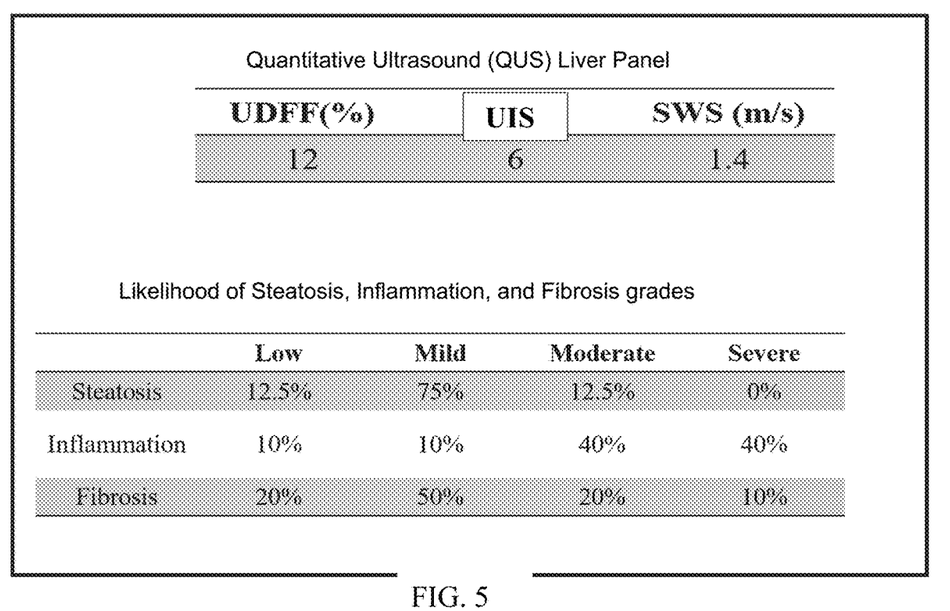
FIG. 5 illustrates another embodiment of a display of relationship to population.

FIG. 5 shows an example. The measured values for the patient are provides as a liver panel. The likelihood of each disease state for each parameter is given. For example, the patient most likely (75%) has mild steatosis, likely (e.g., 40% each) has moderate to severe inflammation, and most likely (e.g., 50%) has mild fibrosis. Other representations of likelihood and/or relationship may be displayed.

FIG. 6 shows one embodiment of a system for parametric ultrasound medical imaging. The system implements the method of FIG. 1 or other methods. Multiple parameters are measured. The values from the measurements are provided with quality indicators and relationship to other patients.

The system includes the transmit beamformer 60, a transducer 62, the receive beamformer 64, a user input 65, an image processor 66, a display 68, and a memory 67. Additional, different or fewer components may be provided. For example, a network interface is provided for interacting with a database and/or computerized patient medical record.

The system is a medical diagnostic ultrasound imaging system. In alternative embodiments, the system is a personal computer, workstation, picture archiving and communications system (PACS) station, or other arrangement at a same location or distributed over a network for real-time or post acquisition imaging.

The transmit and receive beamformers 60, 64 form a beamformer for scanning (e.g., transmit and receive operations) using the transducer 62. Sequences of pulses are transmitted, and responses are received based on operation or configuration of the beamformer. The beamformer scans for measuring fat fraction and imaging tissue.

The transmit beamformer 60 is an ultrasound transmitter, memory, pulser, analog circuit, digital circuit, or combinations thereof. The transmit beamformer 60 is operable to generate waveforms for a plurality of channels with different or relative amplitudes, delays, and/or phasing. Upon transmission of acoustic waves from the transducer 62 in response to the generated electrical waveforms, one or more beams are formed. A sequence of transmit beams are generated to scan a two or three-dimensional region. Sector, Vector®, linear, or other scan formats may be used. The same region may be scanned multiple times using different scan line angles, F numbers, and/or waveform center frequencies. For flow or Doppler imaging and for shear imaging, a sequence of scans along the same line or lines is used. In Doppler imaging, the sequence may include multiple beams along a same scan line before scanning an adjacent scan line. For shear imaging, scan or frame interleaving may be used (i.e., scan the entire region before scanning again). Line or group of line interleaving may be used. In alternative embodiments, the transmit beamformer 60 generates a plane wave or diverging wave for more rapid scanning.

The transducer 62 is an array for generating acoustic energy from electrical waveforms. For an array, relative delays or phasing focus the acoustic energy. A given transmit event corresponds to transmission of acoustic energy by different elements at a substantially same time given the delays.

The transducer 62 is a 1-, 1.25-, 1.5-, 1.75- or 2-dimensional array of piezoelectric or capacitive membrane elements. The transducer 62 includes a plurality of elements for transducing between acoustic and electrical energies. Receive signals are generated in response to ultrasound energy (echoes) impinging on the elements of the transducer 62. The elements connect with channels of the transmit and receive beamformers 12, 16. Alternatively, a single element with a mechanical focus is used.

The receive beamformer 64 includes a plurality of channels with amplifiers, delays, and/or phase rotators, and one or more summers. Each channel connects with one or more transducer elements. The receive beamformer 64 is configured by hardware, firmware, or software to apply relative delays, phases, and/or apodization to form one or more receive beams in response to each imaging transmission. The receive beamformer 64 outputs data representing spatial locations using the receive signals. Relative delays and/or phasing and summation of signals from different elements provide beamformation.

The receive beamformer 64 may include a filter, such as a filter for isolating information at a second harmonic or other frequency band relative to the transmit frequency band. Such information may more likely include desired tissue, contrast agent, and/or flow information. In another embodiment, the receive beamformer 64 includes a memory or buffer and a filter or adder. Two or more receive beams are combined to isolate information at a desired frequency band, such as a second harmonic, cubic fundamental or another band.

In coordination with the transmit beamformer 60, the receive beamformer 64 generates data representing the region. By scanning the region of interest with ultrasound, data (e.g., beamformed samples) is generated. By repeating the scanning, ultrasound data representing the region at different times, frequencies, and/or scan angles is acquired. Different scans may be performed for measuring values of different parameters. One or more scans or frames of data (ultrasound data representing response from the patient at a given time or period) may be used for measuring multiple parameters. The beamformers 60, 64 are configured to scan tissue in a patient using the transducer 62. The scans are for each of the multiple types of parametric ultrasound medical imaging. For example, the liver of a patient is scanned. The quantitative ultrasound and shear wave (e.g., ARFI) scans for estimating fibrosis, inflammation, and fat fraction from ultrasound are performed.

The receive beamformer 64 outputs beam summed data representing spatial locations. Data for a single location, locations along a line, locations for an area, or locations for a volume are output. Dynamic focusing may be provided. Data for different types of measures are acquired with a series of shared or interleaved scans. B-mode or Doppler scanning may be performed separately or using some of the same data. Scanning for parameter estimation may use image data or data acquired for B-mode or Doppler imaging or may use data from a scan just for parameter estimation (e.g., ARFI scanning).

The user input 65 is a keyboard, touch screen, mouse, track pad, sliders, buttons, knobs, roller ball, and/or another computer user input device. The user input 65 in combination with the display 68 is a user interface for user interaction with the system. The user input 65 may be used to trigger parametric scanning. In one embodiment, a single input or activation of the user input 65 triggers scanning for multiple parameters. After interacting with the user interface to configure the system, the scanning is started by the single activation using the user input 65. The beamformers 60, 64 are configured to scan for multiple types of parameters in response to the single activation on the user interface.

The image processor 66 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof, or other now known or later developed device for detecting and processing information for display from beamformed ultrasound samples.

In one embodiment, the image processor 66 includes one or more detectors and a separate image processor. The separate image processor is a control processor, general processor, digital signal processor, application specific integrated circuit, field programmable gate array, network, server, group of processors, combinations thereof, or other now known or later developed device for calculating values of different types of parameters from beamformed and/or detected ultrasound data, for estimating quality of data and/or values of the parameters, and for determining a relationship of parameter values to population or study statistics. The separate image processor is configured by hardware, firmware, and/or software to perform any combination of one or more of acts 12-18 shown in FIG. 1.

The image processor 66 is configured to estimate one or more values for each of multiple types of parameters or tissue properties. The scan data and/or detected data is used to estimate the values of the parameters for one or more locations. Other data may be used as well, such as data from the patient medical record. The values are calculated from the scan data and/or detected data for each of the types of parameters.

The image processor 66 is configured to determine one or more indicators of quality of one or more of the estimated values. One or more indicators of quality may be calculated for each type of parameter. The scan data, detected data, and/or estimated values are used to determine the values of the indicators of quality.

The image processor 66 is configured to generate one or more panels showing the estimated values relative to published values for grades of disease states. Any relationship of the values estimated for the patient to population or study statistics may be used. The panels are alphanumeric text, graphs, charts, maps, or other display information relating the patient values to values of other patients. The relationship is shown for one or more of the parameters.

The image processor 66 is configured to generate an image. For example, the image includes two or more representations of the same tissue based on two or more estimated parameters, such as two or more representations of spatial distribution of a shear wave velocity, fat fraction, inflammation, fibrosis, backscatter, attenuation, non-linearity coefficient, complex modulus, and/or another ARFI or quantitative ultrasound parameter. The image may include non-parametric representations of the tissue, such as B-mode, M-mode, flow or color mode, and/or another type of ultrasound detection. The parameter maps may be presented alone or as an overlay for a region of interest within a B-mode representation. FIG. 2 shows an example image with three parametric maps 22 overlaid on B-mode representations.

The image processor 66 is configured to generate a display of quality indicators and/or population relationships. This display or displays are part of the image, such as the quality indicators 24 of FIG. 2. Alternatively, the quality indicators and/or the population relationships are shown separate from the parametric image and/or each other. The quality indicators and population relationships may be displayed as part of a radiology or medical record report provided with the parametric images.

The image processor 66 operates pursuant to instructions stored in the memory 67 or another memory. The memory 67 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 68 is a device, such as a CRT, LCD, projector, plasma, printer, or other display for displaying one or two-dimensional images or three-dimensional representations. The two-dimensional images represent spatial distribution in an area. The three-dimensional representations are rendered from data representing spatial distribution in a volume. The display 68 is configured by the image processor 66 or other device by input of the data to be displayed, such as one or more images. The display 68 displays an image representing the tissue, such as the liver.

In one embodiment, the display 68 displays the estimated values of multiple different parameters, quality indicators for one or more of the values or parameters, and/or one or more panels reflecting the relationships of one or more of the values of one or more of the parameters to population statistics. For example, an image is displayed. The image includes two or more representations of scanned tissue, one representation provided for each type of parameter. The image also shows one or both of (1) one or more indicators of the quality and (2) one or more panels. The different information is displayed in a same image or may be shown in separate (e.g., sequential) images.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for parametric ultrasound imaging with an ultrasound scanner, the method comprising:
   activating multi-parametric ultrasound imaging of a patient;
   measuring, by the ultrasound scanner, two or more parameters of the multi-parametric ultrasound imaging in response to one instance of the activating;
   generating an image of values of the two or more parameters; and
   displaying a quality indicator for the measuring, the quality indicator labeled as an indicator of quality in the displaying and provided separately from the values of the two or more parameters, the quality indicator comprising a region of interest quality, an acquisition quality, and a measurement consistency quality, the region of interest quality representing quality of placement of a region of interest relative to tissue of the patient, the acquisition quality representing the quality of the acquired scan data for measuring the two or more parameters, and the measurement consistency quality representing the quality of the values of the measured two or more parameters, and displaying a relationship of one or more of the values to a population, the relationship displayed as boxplots of histologic gradings with multiple grades where the one or more values for the patient are referenced to displayed spectra of values for the population of the histologic grading, each spectrum of the spectra being for a different one of the multiple grades and showing the values for the population for the respective grade.

2. The method of claim 1 wherein activating comprises entering, by a user, a single trigger input, and wherein measuring comprises measuring for the two or more parameters in response to the single trigger input.

3. The method of claim 1 wherein measuring comprises interleaving scanning in a first sequence corresponding to a first one of the two or more parameters with scanning in a second sequence corresponding to a second one of the two or more parameters.

4. The method of claim 1 wherein measuring comprises measuring in quantitative ultrasound and in acoustic radiation force ultrasound.

5. The method of claim 1 wherein measuring comprises measuring the two or more parameters for a liver of the patient, and wherein the two or more parameters comprise levels of fibrosis, inflammation, and fat fraction of the liver of the patient.

6. The method of claim 1 wherein measuring comprises measuring the two or more parameters for each of multiple locations in the patient, and wherein generating the image comprises generating the image representing spatial distributions of the two or more parameters.

7. The method of claim 1 wherein displaying the quality indicator comprises displaying the quality indicator as a map representing quality as a function of location.

8. The method of claim 1 wherein generating the image comprises generating the image with two different spatial representations of the two or more parameters, and wherein displaying comprises displaying the quality indicator and/or the relationship as part of the image.

9. The method of claim 1 wherein displaying comprises displaying the relationship of the value of one of the two or more parameters as a probability of membership based on the population.

10. The method of claim 1 wherein displaying comprises displaying the relationship to the population based on a published study for the population.

11. The method of claim 1 wherein measuring comprises measuring for a location in the patient, wherein generating the image comprises generating the image as showing the values in a graph, colorization, and/or alphanumeric text, and wherein displaying comprises displaying the quality indicator as a bar of quality levels.

12. A system for parametric ultrasound medical imaging, the system comprising:
    a transducer;
    a beamformer configured to scan tissue in a patient, with the transducer, the scan being for first and second types of the parametric ultrasound medical imaging;
    an image processor configured to estimate a first value for the first type and a second value for the second type from the scan, to determine first and second indicators of quality of the estimates of the first and second values, respectively, the indicators of quality comprising a region of interest quality, an acquisition quality, and a measurement consistency quality, the region of interest quality representing quality of placement of a region of interest relative to tissue of the patient, the acquisition quality representing the quality of the acquired scan data for measuring the two or more parameters, and the measurement consistency quality representing the quality of the values of the measured two or more parameters, and to generate first and second panels showing the first and second values for the patient, respectively, with respect to and distinguished from published values for grades of disease states, the published values being population values where a relationship of the first and second values for the patient to the population values is shown in the panels and wherein each of the panels include histologic grading comprising distributions with respect to different grades where the first or second value is shown with respect to each of the different grades; and
    a display configured to display the first and second values, the first and second indicators, and the first and second panels.

13. The system of claim 12 wherein the tissue in the patient comprises a liver, and wherein the first and second types comprise two or more of fibrosis, inflammation, and fat fraction.

14. The system of claim 12 wherein the display is configured to display an image showing the first value as part of a first representation of the tissue for the first type and the second value as part of a second representation of the tissue for the second type, and the image showing one or both of (1) the first and second indicators of the quality and (2) the first and second panels.

15. The system of claim 12 further comprising a user interface, wherein the beamformer is configured to scan for both the first and second types in response to a single activation on the user interface.

16. A method for parametric ultrasound imaging with an ultrasound scanner, the method comprising:
    measuring, by the ultrasound scanner, a first tissue property and a second tissue property of a tissue of the patient;

generating an image showing the first and second tissue properties of the tissue;

displaying first and second indicators of reliability of the measuring of the first and second tissue properties, respectively, each of the first and second quality indicators including separate region of interest quality, acquisition quality, and measurement consistency quality, the region of interest quality representing quality of placement of a region of interest relative to tissue of the patient, the acquisition quality representing the quality of the acquired scan data for measuring the two or more parameters, and the measurement consistency quality representing the quality of the values of the measured two or more parameters; and displaying first and second indicators of the measuring of the first and second tissue properties of the tissue of the patient with respect to population statistics, respectively, the first and second tissue properties displayed in relation to the population statistics as boxplots of histologic grading by grade.

17. The method of claim 16 further comprising activating scanning of the patient, the one instance of activating providing for measuring both the first and second tissue properties without further activation.

18. The method of claim 16 wherein the first tissue property comprises fibrosis, and the second tissue property comprises fat fraction.

* * * * *